United States Patent
Omeis et al.

(10) Patent No.: US 7,485,756 B2
(45) Date of Patent: Feb. 3, 2009

(54) CONTINUOUS PROCESS FOR DECARBOXYLATING CARBOXYLIC ACIDS

(75) Inventors: Marianne Omeis, Dorsten (DE); Guenther Koehler, Marl (DE); Manfred Neumann, Marl (DE); Thomas Kuebelbaeck, Duelmen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 11/961,109

(22) Filed: Dec. 20, 2007

(65) Prior Publication Data

US 2008/0214864 A1 Sep. 4, 2008

(30) Foreign Application Priority Data

Dec. 20, 2006 (DE) ............... 10 2006 060 908

(51) Int. Cl.
*C07C 209/00* (2006.01)
(52) U.S. Cl. ..................................... 564/468
(58) Field of Classification Search .............. None
See application file for complete search history.

(56) References Cited

FOREIGN PATENT DOCUMENTS

| EP | 1 586 553 A1 | 10/2005 |
|---|---|---|
| JP | 04-010452 | 1/1992 |
| JP | 2004-114 | 1/2004 |
| WO | WO 00/39098 | 7/2000 |

OTHER PUBLICATIONS

U.S. Appl. No. 11/961,109, filed Dec. 20, 2007, Omeis et al.
U.S. Appl. No. 12/118,884, filed May 12, 2008, Koehler et al.
Mitsunori Hashimoto, et al., "A Novel Decarboxylation of α-Amino Acids. A Facile Method of Decarboxylation by the Use of 2-Cyclohexen-1-One as a Catalyst", The Chemical Society of Japan, Chemistry Letters, pp. 893-896, 1986.
Georges Chatelus, "N° 408.—La Décarboxylation Thermique Des Acides α-Aminés. I,", Memoires Presentes a La Societe Chimique, pp. 2523-2532.

*Primary Examiner*—Paul A Zucker
(74) *Attorney, Agent, or Firm*—Oblon, Spivak, McClelland, Maier & Neustadt, P.C.

(57) ABSTRACT

A continuous process for decarboxylating carboxylic acids proceeds by I.) initially charging a carbonyl compound as a catalyst in a solvent at reaction temperature, to obtain a catalyst solution; II.) metering a carboxylic acid into the catalyst solution as an aqueous solution, aqueous suspension or as a water-comprising solid, to obtain a reaction mixture; and III.) continuously removing a mixture of $CO_2$, solvent, water and a reaction product or mixture of reaction products from the reaction mixture as a vapor.

20 Claims, No Drawings

CONTINUOUS PROCESS FOR DECARBOXYLATING CARBOXYLIC ACIDS

BACKGROUND OF THE INVENTION

1. Field of the Invention

The invention relates to a process for decarboxylating carboxylic acids.

2. Discussion of the Background

The decarboxylation of amino acids is a commonly used process for preparing amino compounds. The resulting amino compounds are in turn starting compounds for numerous industrial intermediates and active pharmaceutical ingredients.

The reaction mechanism for a decarboxylation of amino acids in the presence of ketones as a catalyst is described by Chatelus in Bull. Soc. Chim. Fr., 1964, 2523-2532:

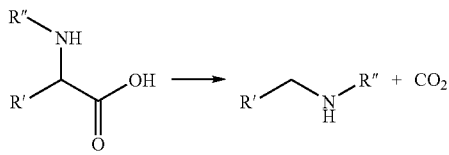

Hashimoto et al. describe, in Chemistry Letters (1986) 893-896, the decarboxylation of α-amino acids using 2-cyclohexen-1-one as a catalyst.

JP 4010452 B also describes a process for decarboxylating amino acids, wherein the amino acid is initially charged in the cyclohexanol solvent and the 2-cyclohexen-1-one catalyst is added.

The processes described in the related art use amino acids as a pure substance. However, these amino acids are frequently available commercially only as aqueous solutions. The recovery of the pure substance from the aqueous solution may, in the individual case, be extremely difficult and laborious. Moreover, the related art processes are batchwise processes.

SUMMARY OF THE INVENTION

It is therefore an object of the present invention to provide a process for decarboxylating carboxylic acids which allows for the use of the carboxylic acids especially the amino acids—as an aqueous solution. In particular, it is an object of the invention to provide a continuous process.

This and other objects have been achieved by the present invention the first embodiment of which includes a continuous process for decarboxylating carboxylic acids of the formula I

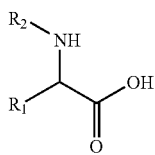

I wherein $R^1$=hydrogen, alkyl, arylalkyl, aryl, cycloalkyl or heterocycle, where the substituent of the $R_1$ type is substituted or unsubstituted, and $R^2$=hydrogen, alkyl, cycloalkyl, said process comprising:

I. initially charging a carbonyl compound as a catalyst in a solvent at reaction temperature, to obtain a catalyst solution;

II. metering a carboxylic acid of said formula I into said catalyst solution as an aqueous solution, aqueous suspension or as a water-comprising solid, to obtain a reaction mixture; and III. continuously removing a mixture of $CO_2$, solvent, water and a member selected from the group consisting of a reaction product of the formula II, a salt which has an anion of the formula III or mixtures thereof

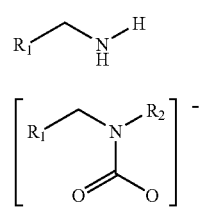

wherein $R_1$ and $R_2$ are defined as in formula I;
from said reaction mixture as a vapor.

DETAILED DESCRIPTION OF THE INVENTION

It has been found that, surprisingly, the carboxylic acid to be decarboxylated can be used as an aqueous solution in the process according to the invention when the carbonyl compound which serves as a catalyst is initially charged in a solvent and the aqueous solution of the carboxylic acid to be decarboxylated is metered in. The mechanism of the decarboxylation is, according to the related art, explained by the Schiff base reaction.

It was all the more surprising that it is possible to use the carboxylic acid to be decarboxylated as an aqueous solution, since Schiff base reactions are known to proceed with elimination of water in order to achieve reaction progress. By means of the process according to the invention, it is now possible to use commercial amino acids, which are available on the market predominantly as an aqueous solution, directly for the decarboxylation, without having to obtain the anhydrous carboxylic acid especially amino acid from the aqueous solution beforehand in a complicated process. At the corresponding reaction temperatures, at which such a decarboxylation generally takes place, the decarboxylation product can be removed from the reaction mixture as vapor together with the $CO_2$, solvent and the water. In this way, it is now possible to provide a continuous process. The desired decarboxylation product can be removed from the reaction zone in vaporous form and be removed in a simple manner as a mixture for example by means of a water separator. The solvent generally forms the organic phase, while the aqueous phase comprises the desired product or a precursor of the desired product. The aqueous phase can now be worked up, for example, by using a thermal separating process.

The invention provides a continuous process for decarboxylating carboxylic acids of the formula I

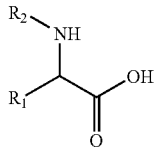

where $R^1$=hydrogen, alkyl, arylalkyl, aryl, cycloalkyl or heterocycle, where the substituent of the $R_1$ type is substituted or unsubstituted, and
$R^2$=hydrogen, alkyl, cycloalkyl, characterized in that
I. a carbonyl compound as a catalyst is initially charged in a solvent at reaction temperature,
II. a carboxylic acid of the formula I is metered into the catalyst in the reaction zone as an aqueous solution, aqueous suspension or as a water-comprising solid, and
III. a mixture of $CO_2$, solvent, water and the desired reaction product of the formula II and/or a salt which has an anion of the formula III

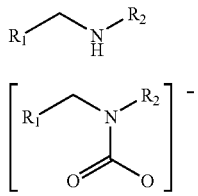

is removed continuously from the reaction mixture as a vapor.

The carboxylic acids used in the process according to the invention are compounds of the general formula I:

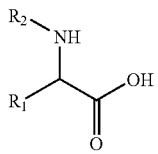

where $R^1$=hydrogen, alkyl, arylalkyl, aryl, cycloalkyl or heterocycle, where the substituent of the $R_1$ type is substituted or unsubstituted, and $R^2$=hydrogen, alkyl, cycloalkyl. As further substituents on the substituent of the $R_1$ type, it may have the following functional groups:

—OH, —COOH, —CONH$_2$, —SH, —S-alkyl, —NH$_2$, —NH—CH(NH$_2$)$_2$, —S—S—CH$_2$—CH(NH$_2$)—COOH, —NH—CO—NH$_2$, —CO—NH-alkyl, —S$^+$(alkyl)$_2$, —SO—CH$_2$—CH=CH$_2$, —O—PO(OH)$_2$.

Mixtures of carboxylic acids may be used.

In particular, naturally occurring amino acids are used in the process according to the invention.

The substituents of the $R_1$ and $R_2$ type may, in a particular embodiment of the process according to the invention, form a ring system. Particular preference is given here to using the naturally occurring amino acid proline or derivatives of proline.

In the process according to the invention, preference is given to using α-amino acids of the formula IV.

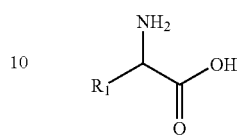

However, preference is given in the process according to the invention to using compounds of the formula V:

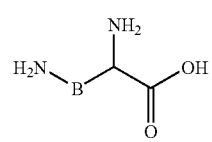

where B -alkyl-, -arylalkyl-, -aryl-, -cycloalkyl- or -heterocycle-. However, preference is given in the process according to the invention to using carboxylic acids of the formula VI

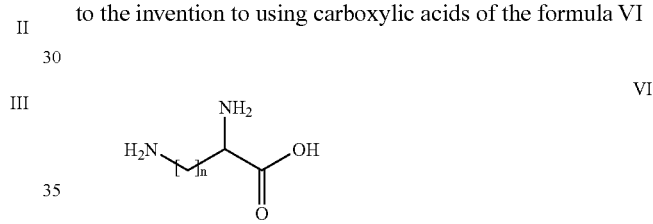

where n=1 to 5. In the process according to the invention, very particular preference is given to using α-amino acids selected from lysine and ornithine.

The carboxylic acids to be decarboxylated may be used in the process according to the invention as an aqueous solution, aqueous suspension or as a water-comprising solid.

In the process according to the invention, for the catalyst, preference is given to using a solvent having a boiling point of 150° C. to 390° C., more preferably of 180° C. to 220° C. The boiling point includes all values and subvalues therebetween, especially including 160, 170, 180, 190, 200, 210, 220, 230, 240, 250, 260, 270, 280, 290, 300, 310, 320, 330, 340, 350, 360, 370 and 380° C. In the process according to the invention, the solvent for the catalyst preferably has a water-entraining action, which means in the context of this invention that the solvent is an azeotroping agent for water. Particular preference is given to using a solvent selected from 2-ethylhexanol, dibenzyltoluene and isononanol in the process according to the invention. A mixture of several suitable solvents may likewise be used as the solvent in the process according to the invention.

As a result of the use of solvent with a high boiling point, a high reaction temperature is possible in the course of metered addition of the aqueous solution of the carboxylic acid during the decarboxylation. As a result, the water which disrupts the reaction mechanism of the decarboxylation and is introduced into the reaction mixture or into the reaction zone as a result of the aqueous administration form of the carboxylic acid is rapidly removed again from the reaction zone of the reactor. In particular, the water is discharged very efficiently when the solvent used in the process according to the invention also has water-entraining action.

The decarboxylation of the process according to the invention is performed preferably at a reaction temperature of 140° C. to 240° C., preferably of 170° C. to 210° C. The reaction temperature includes all values and subvalues therebetween, especially including 150, 160, 170, 180, 190, 200, 210, 220 and 230° C.

The pressure at which the decarboxylation of the process according to the invention is performed is preferably 20 mbar to 2000 mbar, preferably 800 to 1200 mbar and more preferably 950 to 1100 mbar. The pressure includes all values and subvalues therebetween, especially including 50, 100, 200, 400, 600, 800, 1000, 1200, 1400, 1600 and 1800 mbar. Very particular preference is given to performing the decarboxylation of the process according to the invention at atmospheric pressure.

The catalysts used in the decarboxylation of the process according to the invention are preferably high-boiling carbonyl compounds, especially cyclic or acyclic ketones or aldehydes but particular preference is given to using 2-cyclohexen-1-one or isophorone. In the context of this invention, high-boiling carbonyl compounds are understood to mean carbonyl compounds having a boiling point of greater than 150° C.

In the process according to the invention, preference is given to using 0.005 to 10 molar equivalents, preferably 0.007 to 1 molar equivalent, more preferably 0.008 to 0.05 molar equivalent and most preferably 0.009 to 0.03 molar equivalent of catalyst, based on the amount of carboxylic acid used.

In a further embodiment, in the process according to the invention, 0.09 to 4.5 molar equivalents, preferably 0.1 to 1.5 molar equivalents, of catalyst are used, based on the amount of carboxylic acid used.

Owing to the vigorous $CO_2$ evolution during the decarboxylation of the process according to the invention, it is advantageous to add a defoamer to the reaction mixture. In this context, it is possible to use defoamers which behave inertly with respect to the decarboxylation reaction and are familiar to those skilled in the art. Preference is given to using silicone oils. For example, it is possible to use defoamers as sold under the trade name Silikonöl AK 350 or Extran® AP 81.

Preferably, the catalyst is initially supplied to the reaction zone of the reactor together with the solvent.

Subsequently, the catalyst solution is preferably warmed or heated to the desired reaction temperature. Only on attainment of the desired reaction temperature should the aqueous administration form of the carboxylic acid be added. In order to prevent uncontrolled foaming of the reaction mixture as a result of the vigorous $CO_2$ evolution, a defoamer is advantageously added actually before the carboxylic acid is charged to the catalyst solution.

The carbon dioxide which is released in the decarboxylation and is formed in equimolar amounts serves as a stripping gas for the decarboxylation product of the formula II and/or the salt which has an anion of the formula III. It is thus possible that this decarboxylation product can be drawn off from the reaction zone.

$CO_2$, solvent, water and the decarboxylation product are removed from the reaction zone in vaporous form. This product mixture can now be separated into its two phases for example in a water separator. The organic phase, which is generally the solvent, can—especially without further workup be recycled to the reactor. The aqueous phase contains the decarboxylation product of the formula II and/or a salt which has an anion of the formula III. This salt is formed in the vapor phase from the decarboxylation product of the formula II and $CO_2$. In general, after the condensation, a mixture of the decarboxylation product of the formula II and the salt which has an anion of the formula III is present. The aqueous phase is worked up preferably via a thermal process, in which case the removal of the water and also the cleavage of the decarboxylation product of the salt which has an anion of the formula III to the decarboxylation product of the formula II and $CO_2$ can be effected here. The thermal process is preferably performed under inert gas.

The aqueous phase is preferably worked up in an evaporator—for example in a falling-film evaporator, thin-film evaporator or trickle-film evaporator in which case the water is evaporated and the decarboxylation product of the formula II is obtained already in high purity in the bottom of the evaporator—especially a GC purity of >99.0 area %. The GC purity includes all values and subvalues therebetween, especially including 99.1, 99.2, 99.3, 99.4, 99.5, 99.6, 99.7, 99.9 and 100 area %. Under the conditions of the evaporator, the fractions of the decarboxylation product which are present as a salt or as a carbamate can be cleaved back to the desired decarboxylation product of the formula II and $CO_2$ by thermal means. It is advisable to work under inert gas in this workup step in order to prevent reformation of carbamates of the formula III, which can form from the reaction product and $CO_2$ from the atmosphere.

Should the decarboxylation product not be present in the desired purity after the thermal process, it is possible in the process according to the invention for a further distillation or rectification to follow, in order to obtain a highly pure product. This further distillation or rectification step should likewise be effected under inert gas atmosphere, for example nitrogen.

Having generally described this invention, a further understanding can be obtained by reference to certain specific examples which are provided herein for purposes of illustration only, and are not intended to be limiting unless otherwise specified.

EXAMPLES

GC-Measurements

GC-measurements were performed using a HP-5 type column (international nomenclature of GC column types) and a thermal conductivity detector (WLD, thermal conductivity detector TCD). The parameters of operation were:

Injection temperature: 250° C.;
Column temperature (including temperature profile):
50° C., 10K/min;
100° C., 5 min, 20K/min;
250°, 10 min;
Detector temperature: 300° C.
GC purity was determined in area-%.

Example 1

400.0 g of dibenzyltoluene, 8.0 g of isophorone (0.06 mol) and 4.0 g of defoamer (Silikonöl AK 350 silicone oil from Wacker) were initially charged in a 2 l jacketed cylindrical reaction vessel with an internal thermometer, paddle stirrer with a stirred neck and a stirrer motor, a 1 l Telab pump for the metered addition of the aqueous carboxylic acid solution, a 10 cm-long metallized column filled with Raschig rings, a water separator, an attachment for the top temperature and a condenser, and heated with stirring, the oil feed temperature on the thermostat being 240° C. In total, 1195 g of 50% by weight aqueous lysine solution (corresponds to 4.09 mol of L-lysine) were metered into the bottom by means of a pump with a metering rate of 199 g/h.

Water and the cadaverine decarboxylation product were obtained continuously as an aqueous phase on the water separator, while dibenzyltoluene was obtained as the organic phase in the water separator. The aqueous phase (783.5 g) was removed, the cadaverine content of this aqueous phase being 14 area % (determined by means of GC, HP 5 column and TCD detector). The aqueous phase was worked up by means of a thin-film evaporator (height 44 cm, wiper length 38 cm, diameter 5.1 cm, area of the thin-film evaporator: 0.061 m², inert gas purge) at an oil feed temperature of 185° C. and a metering rate of 600 ml/h. In the bottom of the thin-film evaporator, 97.8 g of cadaverine were obtained in a GC purity of >97.0 area % (TCD detector). The yield of cadaverine, based on the L-lysine used was 23.4%.

Example 2

400.0 g of isononanol, 8.0 g of isophorone (0.06 mol) and 4.0 g of defoamer (Silikonöl AK 350 silicone oil from Wacker) were initially charged in a 2 l jacketed cylindrical reaction vessel with an internal thermometer, paddle stirrer with a stirrer neck and a stirrer motor, a 1 l Telab pump for the metered addition of the aqueous carboxylic acid solution, a 10 cm-long metallized column filled with Raschig rings, a water separator, an attachment for the top temperature and a condenser, and heated with stirring. A total of 1368.5 g of a 50% by weight aqueous lysine solution (corresponding to 4.68 mol of L-lysine) were metered into the bottom by means of a pump with a metering rate of 195 g/h.

Water and the cadaverine decarboxylation products were obtained continuously as an aqueous phase on the water separator, while isononanol was obtained as an organic phase in the water separator and recycled into the bottom. The aqueous phase (1049.8 g) was removed, the cadaverine content of this aqueous phase being >30 area % (determined by means of GC, HP 5 column and TCD detector). The aqueous phase was worked up by means of a thin-film evaporator (height 44 cm, wiper length 38 cm, diameter 5.1 cm, area of the thin-film evaporator: 0.061 m², inert gas purge) as an oil feed temperature of 185° C. and a metering rate of 660 ml/h. In the bottom of the thin-film evaporator, 249.0 g of cadaverine were obtained in a GC purity of >99.0 area % (TCD detector). The yield of cadaverine based on the L-lysine used was 52.1%.

According to the color requirement on the cadaverine, there may follow a short-path distillation at standard pressure with introduction of nitrogen or under reduced pressure. 239.5 g of the material obtained at the bottom outlet of the thin-film evaporator was subjected to a fractional distillation at standard pressure with a reflux ratio of 1:1 (bottom temperature 180° C., top temperature 180° C., nitrogen-charged capillary). At the end of the standard pressure distillation, vacuum was applied (bottom temperature 160° C., top temperature 125° C., 130 mbar, reflux ratio 1:1). 227.6 g of colorless clear cadaverine were obtained. This corresponds to a yield of 47.6%. An identity check was effected by $^{13}C$ NMR. The purity of the material was >99%.

German patent application 10 2006 060908.5 filed Dec. 20, 2006, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A continuous process for decarboxylating a carboxylic acid of the formula I

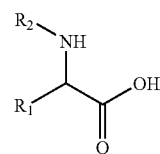

I wherein $R_1$=hydrogen, alkyl, arylalkyl, aryl, cycloalkyl or heterocycle, wherein $R_1$ is substituted or unsubstituted, and $R_2$=hydrogen, alkyl, cycloalkyl, said process comprising:

I. initially charging a carbonyl compound as a catalyst in a solvent at reaction temperature, to obtain a catalyst solution;

II. metering a carboxylic acid of said formula I into said catalyst solution as an aqueous solution, aqueous suspension or as a water-comprising solid, to obtain a reaction mixture; and III. continuously removing a mixture of $CO_2$, solvent, water and a member selected from the group consisting of a reaction product of the formula II, a salt which has an anion of the formula III or mixtures thereof

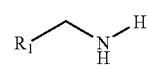

II

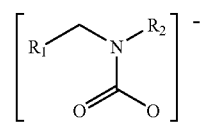

III wherein $R_1$ and $R_2$ are defined as in formula I; from said reaction mixture as a vapor.

2. The process according to claim 1, wherein the solvent has a water-entraining action.

3. The process according to claim 1, wherein the solvent has a boiling point of 150° C. to 390° C.

4. The process according to claim 1, wherein 0.005 to 10 molar equivalents of catalyst based on the amount of carboxylic acid used are used.

5. The process according to claim 4, wherein 0.008 to 0.05 molar equivalent of catalyst based on the amount of carboxylic acid used is used.

6. The process according to claim 1, wherein a defoamer is added to the reaction mixture.

7. The process according to claim 1, wherein a carboxylic acid of the formula

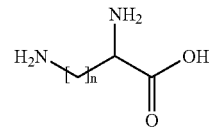

wherein n=1 to 5, is used.

8. The process according to claim 1, wherein $R_1$ is substituted with —OH, —COOH, —CONH$_2$, —SH, —S-alkyl, —NH$_2$, —NH—CH(NH$_2$)$_2$, —S—S—CH$_2$—CH(NH$_2$)—COOH, —NH—CO—NH$_2$, —CO—NH-alkyl, —S$^+$(alkyl)$_2$, —SO—CH$_2$—CH=CH$_2$, or —O—PO(OH)$_2$.

9. The process according to claim 1, wherein said carboxylic acid is a naturally occurring amino acid.

10. The process according to claim 1, wherein $R_1$ and $R_2$ form a ring system.

11. The process according to claim 1, wherein said carboxylic acid is an α-amino acids of the formula IV:

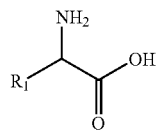

wherein $R_1$ is as defined for formula I.

12. The process according to claim 1, wherein said carboxylic acid is a compound of the formula V:

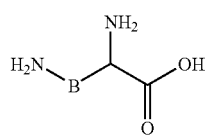

wherein B is -alkyl-, -arylalkyl-, -aryl-, -cycloalkyl- or -heterocycle-.

13. The process according to claim 1, wherein said carboxylic acid is an α-amino acid selected from the group consisting of lysine and ornithine.

14. The process according to claim 1, wherein said solvent is selected from the group consisting of 2-ethylhexanol, dibenzyltoluene, isononanol and mixtures thereof.

15. The process according to claim 1, which is performed at a reaction temperature of 140° C. to 240° C.

16. The process according to claim 1, which is performed at a pressure of 20 mbar to 2000 mbar.

17. The process according to claim 1, wherein said catalyst is a cyclic or acyclic ketone, or a cyclic or acyclic aldehyde.

18. The process according to claim 1, wherein said catalyst is 2-cyclohexen-1-one or isophorone.

19. The process according to claim 1, wherein a decarboxylation product having a GC purity of >99.0 area % is obtained.

20. The process according to claim 1, wherein a mixture of carboxylic acids is used.

* * * * *